United States Patent [19]

Meyer

[11] Patent Number: 5,285,785
[45] Date of Patent: Feb. 15, 1994

[54] APPARATUS AND METHOD FOR LOCATING FOREIGN BODIES IN HUMANS AND ANIMALS

[76] Inventor: Seymour W. Meyer, 495 E. Shore Rd., Great Neck, N.Y. 11024

[21] Appl. No.: 965,186

[22] Filed: Oct. 23, 1992

Related U.S. Application Data

[63] Continuation-in-part of Ser. No. 784,597, Oct. 30, 1991, abandoned.

[51] Int. Cl.$^5$ .............................................. A61B 6/12
[52] U.S. Cl. .................... 128/653.1; 378/164; 33/512
[58] Field of Search ......................... 128/653.1; 378/162-165; 606/130; 33/512, 483, 493, 494

[56] References Cited

U.S. PATENT DOCUMENTS

| | | | |
|---|---|---|---|
| 3,836,776 | 9/1974 | Gullekson | 378/163 |
| 3,848,136 | 11/1974 | Seldin | 378/164 |
| 4,349,917 | 9/1982 | Moore | 378/164 |
| 4,394,770 | 7/1983 | La Franka | 378/164 |
| 4,506,676 | 3/1985 | Duska | 378/165 |
| 4,583,538 | 4/1986 | Onik et al. | 606/130 |
| 4,742,619 | 5/1988 | Swanson | 33/494 |
| 4,764,948 | 8/1988 | Hurwitz | 378/165 |
| 4,860,331 | 8/1989 | Williams et al. | 33/512 |
| 4,953,193 | 8/1990 | Robinson | 378/165 |
| 5,002,735 | 3/1991 | Alberhasky et al. | 378/164 |
| 5,020,088 | 5/1991 | Tobin | 378/164 |
| 5,052,035 | 9/1991 | Krupnick | 378/164 |
| 5,056,228 | 10/1991 | Yamamoto et al. | 33/494 |
| 5,105,457 | 4/1992 | Glassman | 378/164 |
| 5,216,700 | 6/1993 | Cherian | 378/163 |

Primary Examiner—Lee S. Cohen
Assistant Examiner—K. M. Pfaffle
Attorney, Agent, or Firm—Schweitzer Cornman & Gross

[57] ABSTRACT

A method and apparatus for assisting in the location and surgical removal of foreign bodies embedded in the human or animal body. A calibrated grid-forming screen, of a material opaque to X-radiation, is located over the injury site, with accurate reference to a targeting mark naturally or artificially formed near the site. An X-ray image is formed, showing the body part, the foreign object, and a calibrated grid overlay image. Two such images, taken from different angles, typically 90°, enable the precise location of the object to be determined in three dimensions by triangulation. With the location of the foreign body in three dimensions, the surgeon is then able to exactly locate the site for incision and to know in advance the depth to which to extend the incision, and to exactly reach the foreign body. The grid-forming screen may be of thin sheet stainless steel, tin-lead, or lead-plated copper, formed with integral, narrow linear elements extending longitudinally and transversely and intersecting to form a calibrated grid of uniform open squares. The screen also has a central open area, formed with a targeting element to facilitate accurate positioning of the screen in relation to the targeting mark, this being the point of entry of the foreign body or an artificially selected point of entry, marked by pen, to be a guide to locating the foreign body. Extraordinary savings in time and effort by the surgeon are possible using the invention, with corresponding benefits to the patient.

13 Claims, 6 Drawing Sheets

APPARATUS AND METHOD FOR LOCATING FOREIGN BODIES IN HUMANS AND ANIMALS

This is a Continuation-In-Part Application of U.S. patent application Ser. No. 784,597, filed Oct. 30, 1991, now abandoned.

BACKGROUND AND SUMMARY OF THE INVENTION

One of the most common injuries sustained by humans and animals is the accidental penetration of the skin by foreign objects, such as pieces of metal, glass, wood, needles, pencil lead, bullets, BB pellets, nails, screws, fiberglass, paints and pigments. When part of the foreign body still protrudes outside the skin it can be removed fairly easily. However, when the foreign body has penetrated the skin with substantial projectile velocity so that it is completely embedded beneath the skin in deeper tissues, removal is often difficult. This is due to the fact that there may be variation in the direction and depth to which the foreign body has traveled. The presence of the entry wound is of help. When the entry wound is completely healed, locating the object becomes more difficult.

Utilizing currently available materials and techniques, a surgeon can encounter a great deal of difficulty in finding small embedded objects, often spending as much as one half to one and a half hours, or even longer, in the attempt to locate and remove the foreign body. This is true, even though pre-operative X-rays are taken in an effort to localize the position of the object.

Because of the difficulties described above, many surgeons, veterinarians, and podiatrists require fluoroscopic studies to be done in the operating room during the removal procedures. These often are long, drawn-out procedures, which undesirably subject the patients to prolonged anesthesia and excessive X-ray exposure.

Using the device and method of the invention, a pre-operative X-ray study is made of the traumatized area, to precisely pinpoint the location of the foreign body and allow the surgeon thereafter to quickly effect its removal, often reducing to a few minutes procedures heretofore requiring extensive time, patience and effort.

The invention is a novel grid-like screen, formed of a material opaque to X-rays, preferably thin stainless steel but also tin-lead or lead-plated copper, and the method of use of the screen. When a patient presents a history to a doctor suggesting the possible presence of an embedded foreign body, an X-ray is taken to verify its presence or absence. If its presence is confirmed, then the invention comes into play. The screen is carefully placed over the anatomic part with a targeting element directed over the point of injury or entry wound or a marked point, these constituting a targeting mark. It is held in this position or taped in place. The anatomic part is then turned or manipulated so that the screen rests against the cassette holding the film. An X-ray image is taken, which will incorporate the grid pattern and fix the location of the foreign object with respect thereto in a two-dimensional plane. The screen is then re-positioned at right angles to its first orientation with the targeting element again aligned with the previously selected injury or marked point, and a second X-ray image is taken with the screen again positioned against the film cassette. These two X-ray images are used by the surgeon to triangulate the location of the foreign body, and determine and mark where the incision should be made in order to retrieve it. The surgeon can then quickly effect its removal. If, under certain circumstances, it is not possible to manipulate the anatomic part so that the screen rests directly against the film cassette, then the screen can rest between the X-ray source and the anatomic part. This is not the preferred method.

For a more complete understanding of the above and other features and advantages of the invention, reference should be made to the following detailed description of a preferred embodiment and to the accompanying drawings.

DESCRIPTION OF A PREFERRED EMBODIMENT

Figure 1:
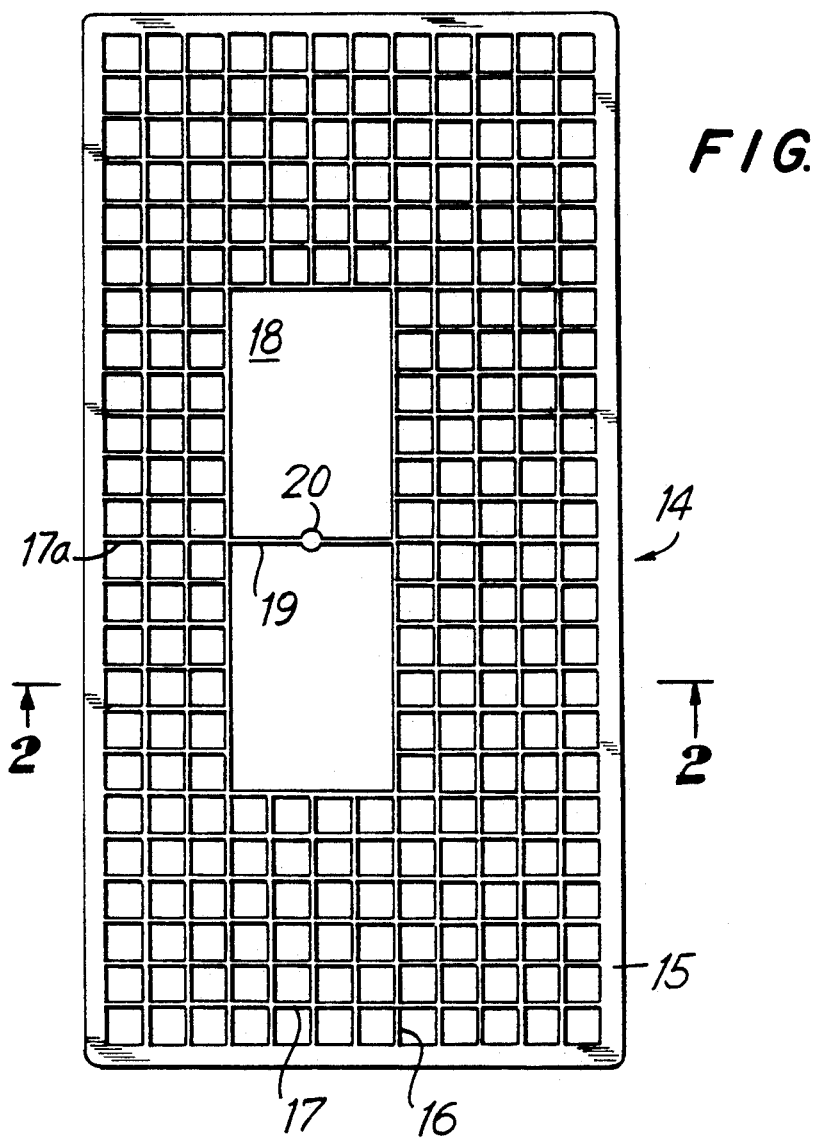
FIG. 1 is a plan view of a grid-like screen embodying my invention.
Figure 2:
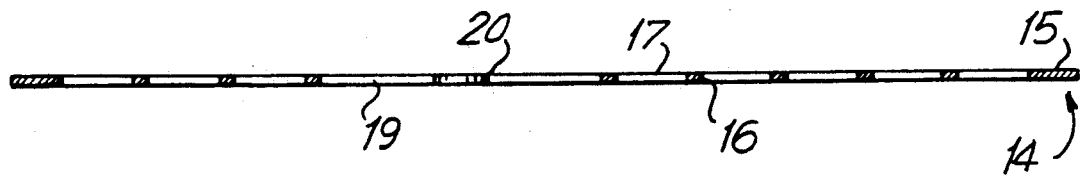
FIG. 2 is an enlarged side elevational cross-sectional view taken along lines 2—2 of FIG. 1.
Figure 3:
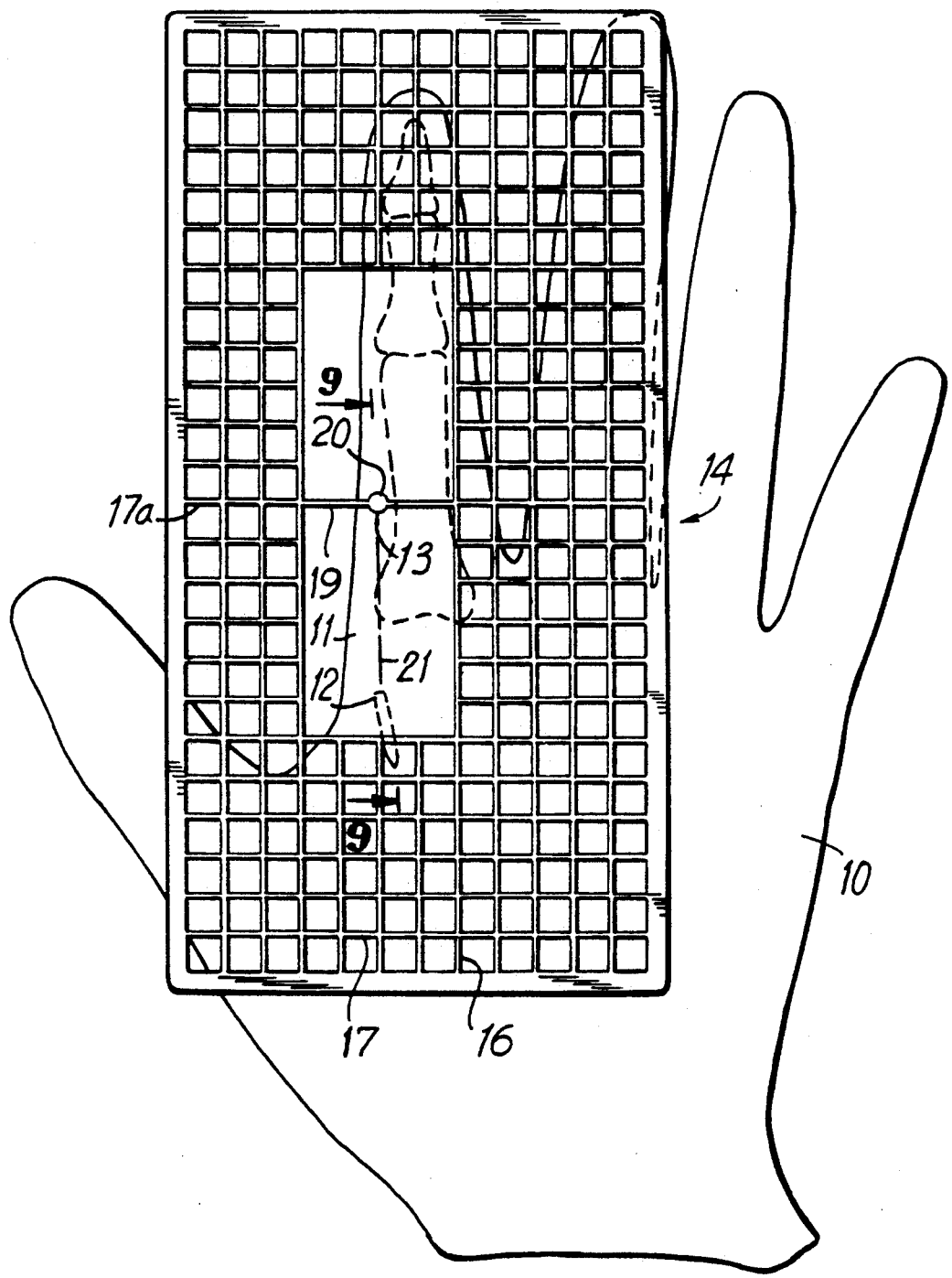
FIG. 3 is a plan view of a patient's hand with an embedded foreign body, illustrating the use of the positioning of the screen over the palm of the hand.
Figure 8:
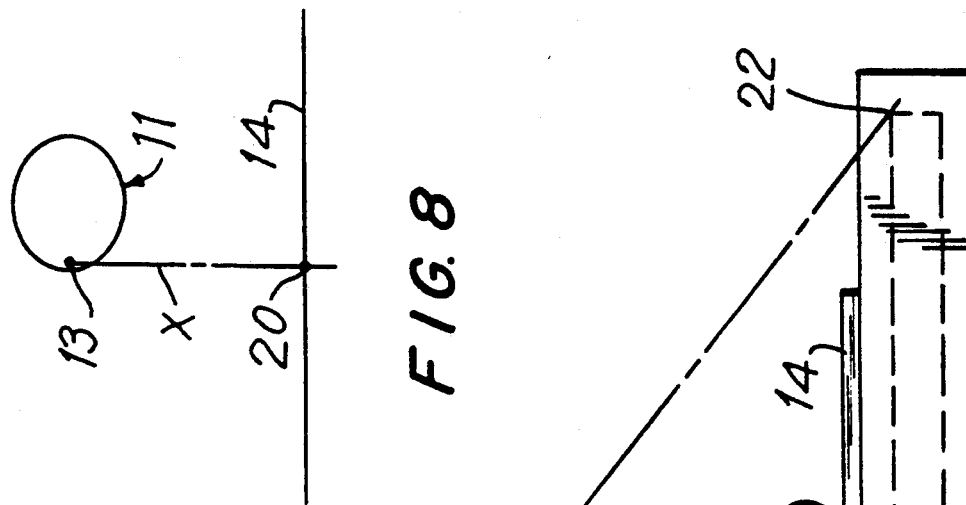
FIG. 8 is a schematic cross-sectional view of the finger of FIG. 6, taken at the level of the point of entry, to show the tangential alignment of the targeting mark with the screen targeting element positioned for the second X-ray image.
Figure 5:
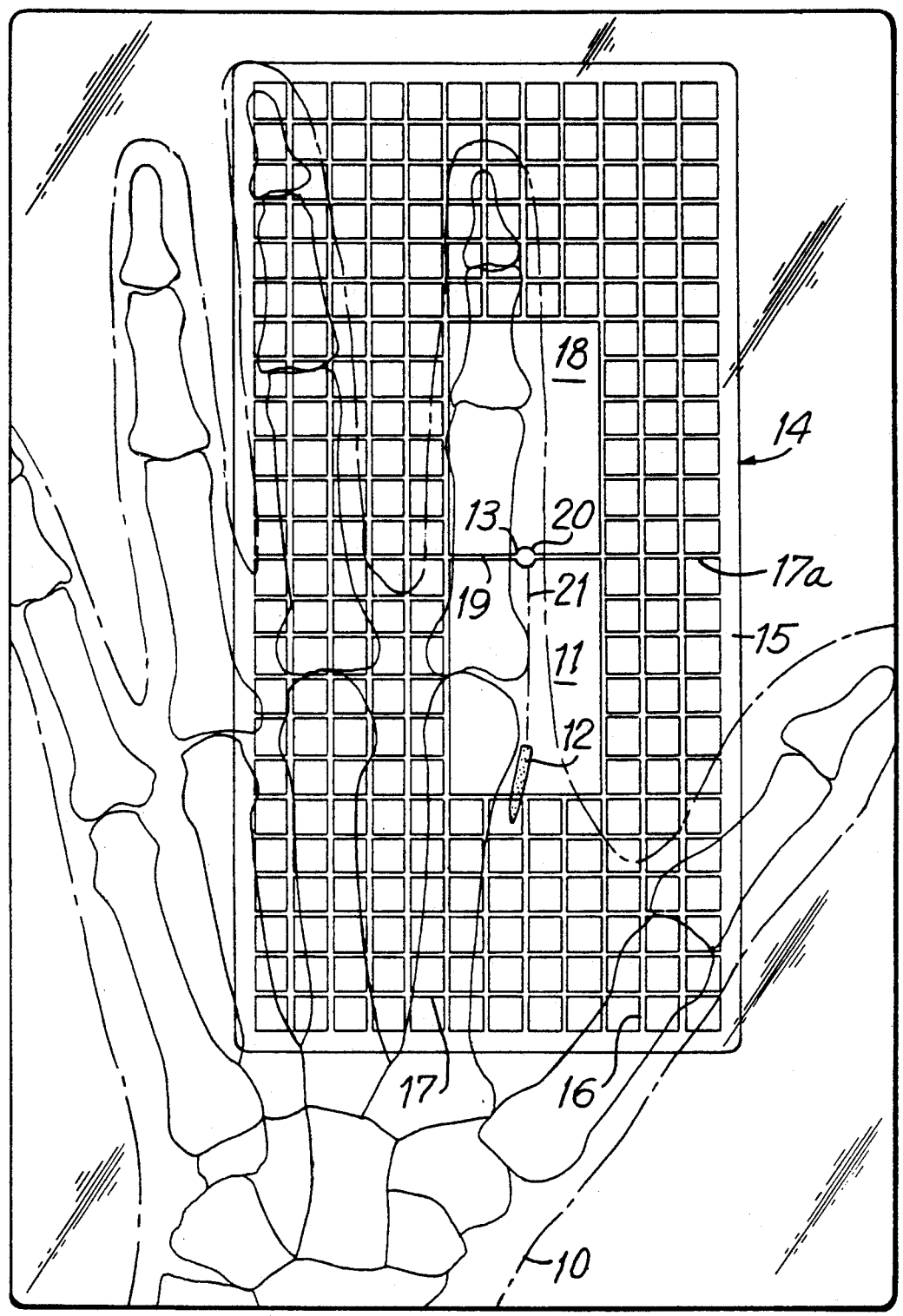
FIG. 5 is a plan view of an X-ray film copy resulting from the exposure in an antero-posterior position and showing the foreign body and the targeting element in a two-dimensional relationship.
Figure 9:
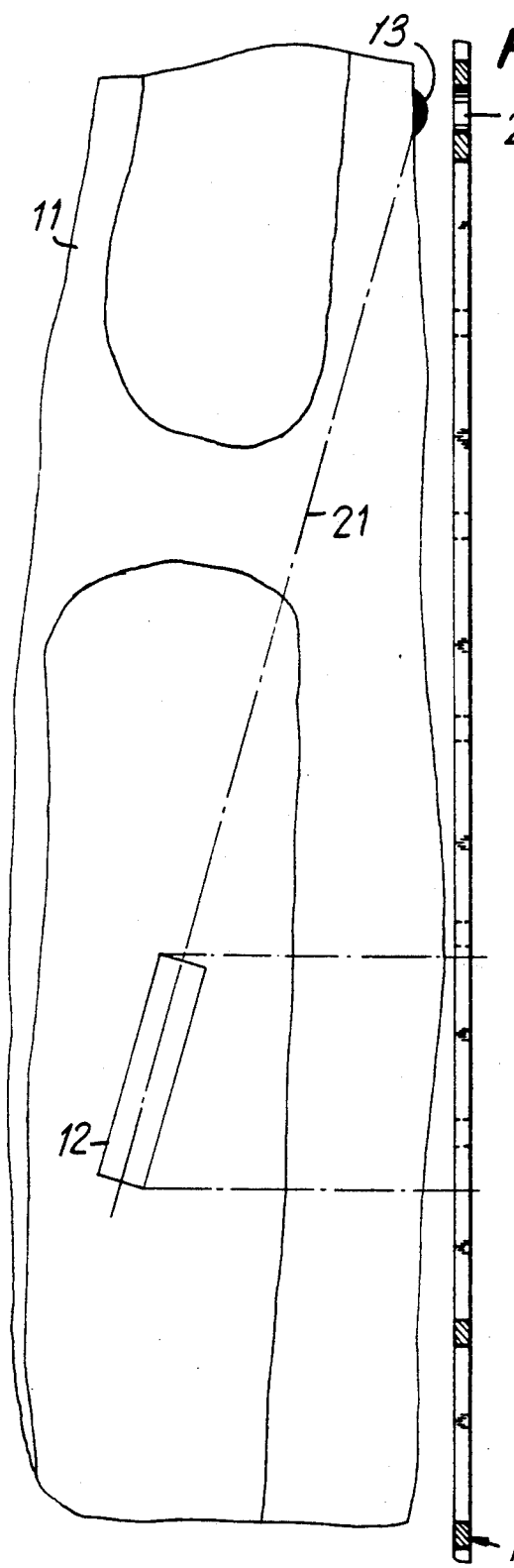
FIG. 9 is a greatly enlarged fragmentary cross-sectional view as taken generally along line 9—9 of FIG. 3.

Referring now to the drawings, and more particularly to FIGS. 1-3, the reference numeral 10 designates a patient's hand, the index finger 11 of which contains an embedded foreign body 12. In the illustration, the foreign object is in the form of a rod-like element which has entered the finger 11 near the second joint, leaving an observable entry wound 13, and has travelled a considerable distance along a path 21 (FIGS. 3 and 5) before coming to rest.

To assist the surgeon is locating the position of the object, the invention provides a novel grid-like screen 14, (FIGS. 1 and 2) formed of a material opaque to X-rays, which can be placed over the injury site, in this case the patient's hand 10. The opacity of the material to X-radiation must be sufficient that the grid pattern is clearly visible in an X-ray image of the hand taken through the grid. Stainless steel sheet, formed into a grid-like screen, is an ideal material for this purpose. Variations include tin-lead or lead-plated copper. The optimum dimensions, thickness, and grid size are a function of the area to be imaged. For the hand, suitable screen dimensions are about 3¼" by 6¼", with a minimal thickness of about 2 mils, and preferably 0.06", and a grid pattern of ¼" squares. For other injury sites, other configurations may be appropriate. For arms, legs and thighs, for example, a larger screen, with a ½" grid pattern, may be more suitable. For the neck, chest and abdomen, a still larger screen may be desired. The thickness of the screen may vary so that it may be visualized on an X-ray when used with any part of the anatomy.

The grid screen 14 advantageously is formed with a strengthening border 15 about its periphery. Grid elements 16, 17 project longitudinally and transversely within the border, at a uniform spacing to form a calibrated grid of small, uniform squares. The grid elements 16, 17 desirably are as narrow as practicable, consistent with structural integrity, to maximize the unobstructed area while at the same time forming a readily visible image on the X-ray exposure.

To particular advantage, the grid-like screen is formed with a rectangular opening 18 in its central region, which is free of the grid elements, to facilitate positioning the target point in relation to the point of entry or targeting point. The opening 18 is bisected by a central transverse grid element 17a, which extends across the full width of the screen and forms a positioning element 19. The positioning element desirably incorporates a targeting device 20, which may advantageously take the form of a small diameter solid circle, which is placed directly over the point of entry. Alternatively, it may take the form of a small diameter circular eye.

While not illustrated, a longitudinal grid element may extend across the length of the opening, meeting the element 17a at the targeting device 20. This may give greater rigidity to the device.

Although the rectangular opening 18 may be centrally located, it is more advantageously offset slightly to one side. The irregularity in the positioning of the rectangle helps locate the foreign body with respect to a medial or lateral location. By medial we mean closer to the body, and by lateral away from the body. This enables the screen to be flipped over, from one side to the other, if desired, to obtain a more favorable positioning on the opening in relation to the injury site.

In the device specifically illustrated herein, a screen suitable for examination of hand and foot injuries is formed with a 12 by 24 grid structure, with a rectangular opening measuring 4 by 12 grid squares.

Figure 4:
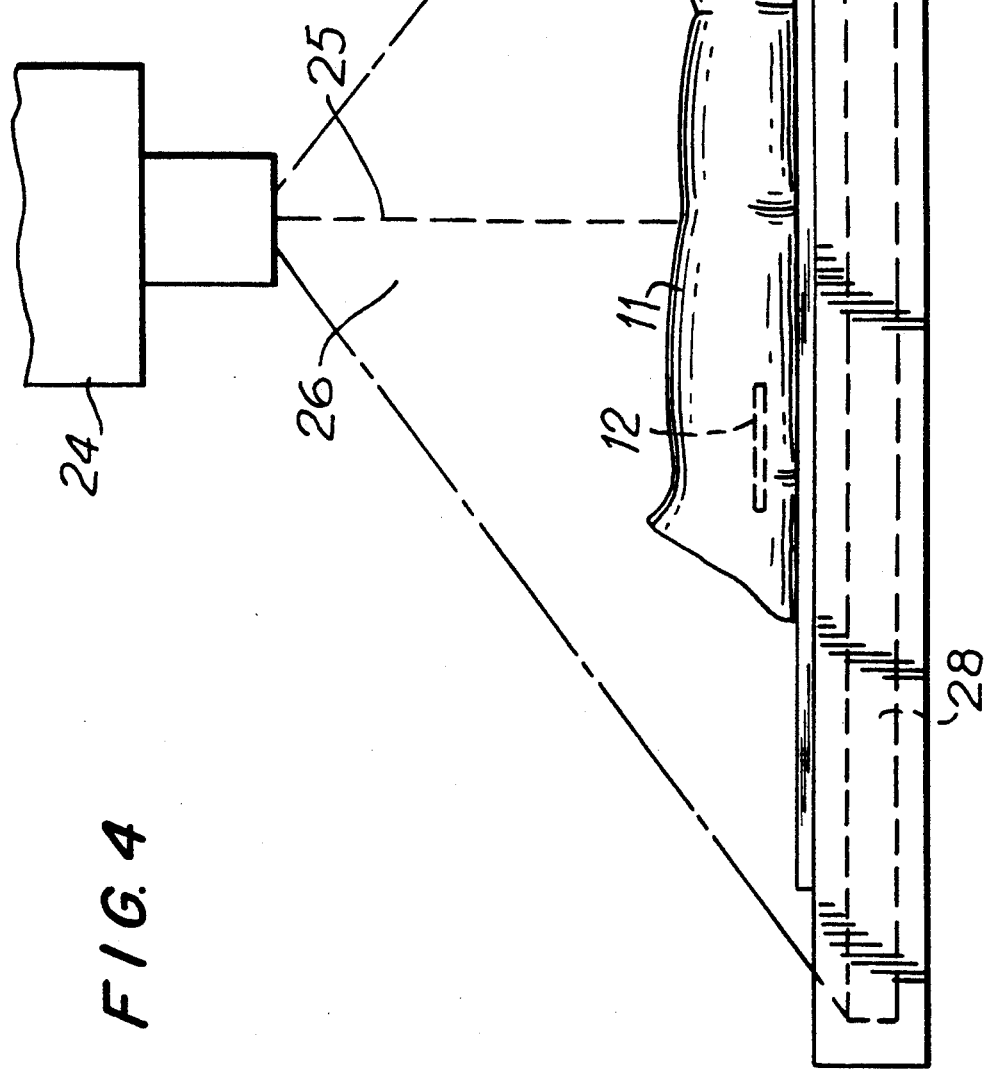
FIG. 4 is a side elevational, schematic view showing the relational placement of the X-ray source, the anatomical part, the screen, and the X-ray film cassette while the X-ray is being taken.

In the method of the invention, as exemplified by studies of the hand injury shown in the drawings, the grid screen 14 is initially supported directly over the hand, generally in the manner shown in FIG. 3. The screen can be supported directly on the hand by the surgeon or by application of adhesive tape. The targeting element 20 is carefully aligned with the point of entry or targeting point, sometimes referred to as a targeting mark. Thus the location of the screen is predetermined with respect to the targeting mark. Where the entry wound is visible, as at 13 (FIG. 5) in the illustration, the entry wound forms the targeting mark, and the targeting circle or eye advantageously is aligned directly over the wound. The hand is then turned or rotated so that the screen directly abuts the X-ray film cassette 22. As seen in FIG. 4, the X-ray apparatus has an X-ray source 24 with a principal axis 25 which emits a stream of X-rays 26 first passing through the hand 10 containing the foreign body 12. The rays then penetrate the screen 14, and finally the cassette 22 containing unexposed film 8. The resulting X-ray image, incorporating the calibrated grid overlay image formed by the image of the screen, will precisely locate the position of the embedded foreign body 12 in a two-dimensional sense, in relation to the grid overlay and to the targeting mark.

Figure 6:
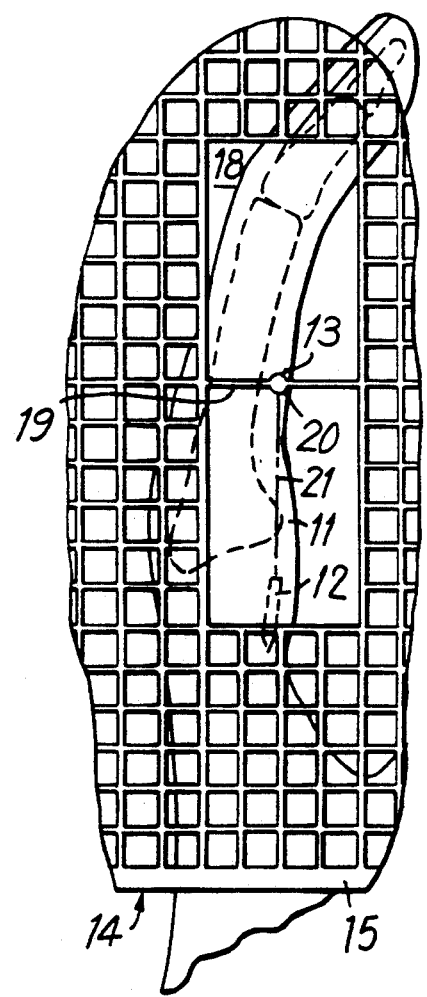
FIG. 6 is a plan view showing the patient's finger reoriented at right angles with respect to its position in FIG. 3 thus constituting a medio-lateral view.

After completion of the first image, the plane of the patient's hand is reoriented approximately 90°, relative to the X-ray apparatus (FIG. 6). To accomplish this, the hand is carefully turned with the targeting mark remaining in an imaginary, perpendicular line x extending upwardly from the targeting element 20. Accordingly, with respect to the grid-forming screen, the repositioned hand is oriented substantially at right angles to original orientation used in taking the first image. Thus the screen is moved to a second predetermined location with respect to the targeting mark.

Figure 7:
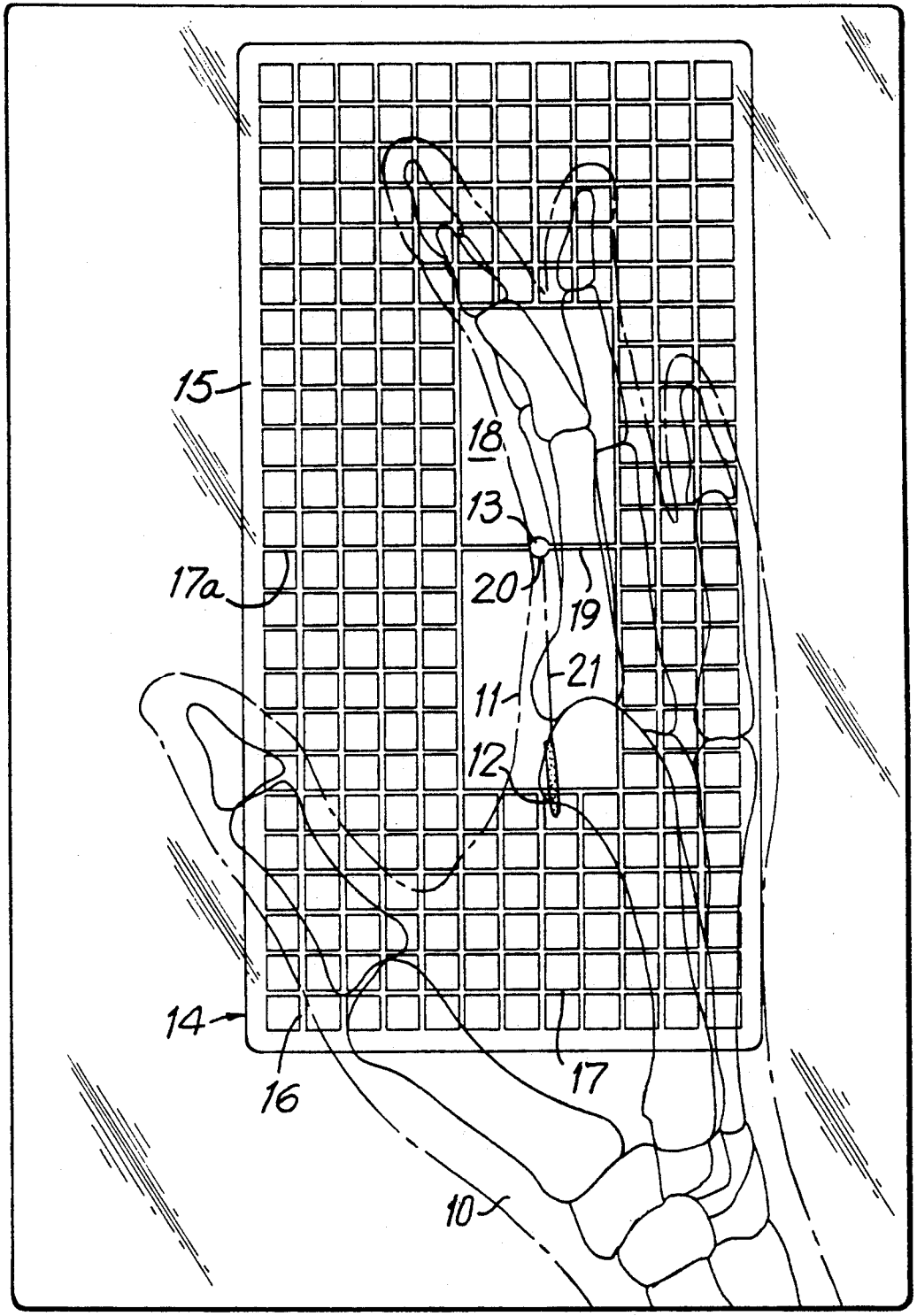
FIG. 7 is a plan view of an X-ray film resulting from the exposure in the medio-lateral position of FIG. 6 and showing the foreign body and the targeting element in a two-dimensional relationship, at right angles to that shown in FIG. 5.

The second X-ray exposure taken in accordance with the procedure of the invention, results in an image (FIG. 7) corresponding to the illustration of FIG. 6. The foreign body 12 is precisely and measurably located with respect to the overlay image of the grid structure. This presents a two-dimensional relationship showing the depth of the foreign body.

As shown particularly in FIG. 6, in aligning the grid screen 14 for the second image, the targeting circle or eye must be aligned tangentially with the targeting mark, in this case the entry wound 13. This enables accurate correlation of the images, one with respect to the other, so that the location of the foreign object may be precisely pinpointed in three dimensions. Accordingly, from the two images thus obtained, the surgeon may quite precisely identify the optimum site for a surgical incision and the required depth of the incision. Experience with the new procedure establishes that the location and removal of the foreign object may be completed in far less time than with conventional procedures and with correspondingly less trauma to the patient, both in terms of surgical damage and of time and dosage of anesthesia.

The surgeon must work with the X-ray technician in the taking of the films so that as he visualizes the two films at right angles to each other he can better correlate these films and know exactly where to make the incision and how deep he must go in order to come upon the foreign body.

In cases where the entry wound is healed or otherwise not detectable, the surgeon selects an appropriate point near the desired targeting site, potentially near the possible site of entry, and forms a targeting mark on the patient's skin with a suitable permanent marking pen or surgical pen. The targeting circle or eye 20 is then aligned with the surgeon's mark to achieve desired alignment of the respective grid images.

In many instances, the location of the embedded foreign object will fall within the rectangular opening 18. This does not present a problem, however, as the adjacent grid lines may be manually or otherwise projected across the opening with required accuracy when performing analysis and measurements from the finished images. In certain cases, there are observational advantages to be derived from positioning the rectangular opening to include the expected site of the foreign object. Very small objects, in particular, will thus not be masked by the grid elements.

In certain circumstances it may prove necessary to take an X-ray in which the screen is positioned between the body part and the X-ray source. For example, if a patient is not capable of being turned or rotated, the X-ray would be taken in this manner. The X-ray source would then be rotated for a second x-ray. This is not the preferred method and may present certain difficulties. The further the grid is from the film, the more likely the resulting grid pattern will be distorted. The surgeon will have to make accommodations when planning the incision to compensate for the resulting distortion.

The procedure of the invention requires an absolute minimum of additional equipment. A suitable selection of simple grid screens, appropriate for various injury sites, is all that is necessary. Yet the benefits realized are extraordinary indeed. The removal of small bodies or objects, deeply embedded in the body can be extremely difficult and time consuming, even with the aid of conventional pre-operative X-ray images. With the device and procedure of the invention the object can be precisely located in the body, and an optimum incision site and surgical technique can be pre-planned. As a result, the time required to find and remove the object typically is reduced to a fraction of that conventionally needed. Further, the invention may be used for humans or animals.

The device and procedure of the invention are characterized by simplicity and economy, yet the results achieved are truly remarkable in terms of minimizing both surgical effort and patient trauma.

It should be understood, of course, that the specific form of the invention herein illustrated and described is intended to be representative only, as certain changes may be made therein without departing from the clear teachings of the disclosure. Accordingly, reference should be made to the following appended claims in determining the full scope of the invention.

I claim:

1. A grid-like screen device for use in assisting the location of foreign bodies in the human or animal body for subsequent surgical removal, which comprises:
   (a) a generally flat, planar sheet-like member formed of thin material,
   (b) said material being sufficiently opaque to X-radiation to form an overlay image when interposed between an X-ray film cassette and an injury site being X-rayed;
   (c) said sheet-like member being formed over a substantial portion of its surface with a calibrated grid of open rectangles, defined by integral, narrow, linear grid-forming elements of said material intersecting with each other at right angles to form individual open rectangles;
   (d) said sheet-like member being formed with a generally centralized open area defined by edges and substantially free of linear grid-forming elements;
   (e) the edges of said open area being defined by certain of said linear elements; and
   (f) at least two of the linear elements, forming at least two of the edges of said open area, being intersected by at least one grid-forming linear element extending at right angles thereto.

2. A grid-like screen device according to claim 1, further characterized by,
   (a) an integral targeting element on one of said grid-forming elements to facilitate alignment of said screen device with respect to a predetermined point on said body.

3. A grid-like screen device according to claim 2, further characterized by,
   (a) said targeting element being formed in part by at least one of said grid-forming linear elements extending transversely across said open area and substantially bisecting said open area.

4. A grid-like screen device according to claim 1, further characterized by,
   (a) said screen being formed of thin, sheet stainless steel.

5. grid-like screen according to claim 1, further characterized by,
   (a) said screen being formed of tin-lead.

6. A grid-like screen device according to claim 1, further characterized by,
   (a) said screen being formed of lead-plated copper.

7. A grid-like screen device according to claim 1, further characterized by,
   (a) said screen being rectangular in form;
   (b) certain of said linear elements extending longitudinally of said screen and being uniformly spaced apart in the transverse direction,
   (c) others of said linear elements extending transversely of said screen and being uniformly spaced apart in the longitudinal direction to form a grid of open squares.

8. A grid-like screen according to claim 7, further characterized by,
   (a) said screen having a generally centralized but asymmetrically positioned rectangular open area generally free of linear grid-forming elements;
   (b) a transversely extending linear grid-forming element extending across said open area;
   (c) said last-mentioned linear grid-forming element including a targeting element to assist in the positioning of said screen.

9. A grid-like screen according to claim 8, further characterized by,
   (a) said targeting element comprises a small circular opening formed in said first-mentioned grid-forming linear element.

10. A grid-like screen according to claim 8, further characterized by,
    (a) said targeting element comprises a small circle formed in said last-mentioned, grid-forming, linear element.

11. A grid-like screen device for use in assisting the location of foreign bodies in the human or animal body for subsequent surgical removal, which comprises
    (a) a generally flat, planar sheet-like member formed of thin material,
    (b) said material being sufficiently opaque to X-radiation to form an overlay image when interposed between an X-ray apparatus and an injury site being X-rayed,
    (c) said sheet-like member being formed over a substantial portion of its surface with a calibrated grid of open rectangles, defined by integral, narrow, linear grid-forming elements of said material intersecting with each other at right angles to form individual open rectangles,
    (d) said sheet-like member being formed with a generally centralized open area defined by edges substantially free of linear grid-forming elements,
    (e) the edges of said open area being defined by certain of said linear elements, and
    (f) at least two of the linear elements, forming at least two of the edges of said open area, being intersected by said linear grid-forming elements extending at right angles thereto.

12. A grid-like screen device for use in assisting the location of foreign bodies in the human or animal body for subsequent surgical removal, which comprises
   (a) a generally flat, planar sheet-like member formed of thin material,
   (b) said material being sufficiently opaque to X-radiation to form an overlay image when interposed between an X-ray apparatus and an injury site being X-rayed,
   (c) said sheet-like member being formed over a substantial portion of its surface with a calibrated grid of open rectangles, defined by integral, narrow, linear grid-forming elements of said material intersecting with each other at right angles to form individual open rectangles,
   (d) an integral targeting element extending into said open area to facilitate alignment of said screen device with respect to a predetermined point on said body, and
   (e) said targeting element being formed in part by said linear grid-forming elements extending transversely across said open area and substantially bi-secting said open area longitudinally.

13. A grid-like screen device for use in assisting the location of foreign bodies in the human or animal body for subsequent surgical removal, which comprises
   (a) a generally flat, planar sheet-like member formed of thin material,
   (b) said material being sufficiently opaque to X-radiation to form an overlay image when interposed between an X-ray apparatus and an injury site being X-rayed,
   (c) said sheet-like member being formed over a substantial portion of its surface with a calibrated grid of open rectangles, defined by integral, narrow, linear grid-forming elements of said material intersecting with each other at right angles to form individual open rectangles,
   (d) said screen having a generally centralized, but asymmetrically positioned rectangular open area generally free of linear grid-forming elements,
   (e) a transversely extending linear grid-forming element extending across said open area, and
   (f) said last-mentioned linear grid-forming element including a targeting element to assist in the positioning of said device.

* * * * *